US011575080B2

(12) United States Patent
Shimizu et al.

(10) Patent No.: US 11,575,080 B2
(45) Date of Patent: Feb. 7, 2023

(54) PIEZOELECTRIC MEMBER, ULTRASONIC OSCILLATION ELEMENT, ULTRASONIC PROBE, ULTRASOUND DIAGNOSTIC SYSTEM, AND METHOD FOR PRODUCING PIEZOELECTRIC MEMBER

(71) Applicant: KONICA MINOLTA, INC., Tokyo (JP)

(72) Inventors: Naoki Shimizu, Hachioji (JP); Kazunari Tada, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 809 days.

(21) Appl. No.: 16/484,141

(22) PCT Filed: Mar. 5, 2018

(86) PCT No.: PCT/JP2018/008313
§ 371 (c)(1),
(2) Date: Aug. 7, 2019

(87) PCT Pub. No.: WO2018/164047
PCT Pub. Date: Sep. 13, 2018

(65) Prior Publication Data
US 2019/0363242 A1 Nov. 28, 2019

(30) Foreign Application Priority Data
Mar. 6, 2017 (JP) .............. JP2017-042265

(51) Int. Cl.
*H01L 41/047* (2006.01)
*H01L 41/08* (2006.01)
(Continued)

(52) U.S. Cl.
CPC ............ *H01L 41/08* (2013.01); *A61B 8/4444* (2013.01); *A61B 8/4494* (2013.01);
(Continued)

(58) Field of Classification Search
CPC ...... H01L 41/08; H01L 41/047; H01L 41/193
See application file for complete search history.

(56) References Cited

U.S. PATENT DOCUMENTS

2013/0264109 A1* 10/2013 Kamakura ............. H05K 3/301
29/832
2014/0292156 A1 10/2014 Kashiwaya
2014/0339962 A1* 11/2014 Furukawa ........... H01L 41/1873
310/363

FOREIGN PATENT DOCUMENTS

DE 102008048051 A1 4/2010
JP S57126125 A 8/1982
(Continued)

OTHER PUBLICATIONS

International Search Report (PCT/ISA/210) dated May 1, 2018, by the Japan Patent Office as the International Searching Authority for International Application No. PCT/JP2018/008313.
(Continued)

*Primary Examiner* — J. San Martin
(74) *Attorney, Agent, or Firm* — Buchanan Ingersoll & Rooney PC

(57) ABSTRACT

A piezoelectric member including metal electrodes with improved adhesiveness to piezoelectric elements is to be provided. A piezoelectric member 102 includes a piezoelectric element 21, and a pair of electrodes 41, 42 respectively formed on a pair of opposing surfaces 21b, 21c of the piezoelectric element 21. The electrodes 41, 42 includes: a base film 41a that is formed on the opposing surfaces 21b, 21c of the piezoelectric element 21 and contains a thiol group; a metal adhesive film 41b formed on the base film 41a; and an electrode film 41c that is formed on the metal adhesive film 41b and is for applying voltage to the piezo-
(Continued)

electric element 21. The metal adhesive film 41*b* is formed with a different material from the electrode film 41*c*, and has a thickness of 1 to 10 nm.

20 Claims, 7 Drawing Sheets

(51) Int. Cl.
*A61B 8/00* (2006.01)
*H01L 41/193* (2006.01)
*H01L 41/33* (2013.01)

(52) U.S. Cl.
CPC .......... *H01L 41/047* (2013.01); *H01L 41/193* (2013.01); *H01L 41/33* (2013.01)

(56) References Cited

FOREIGN PATENT DOCUMENTS

| | | | |
|---|---|---|---|
| JP | 2011155574 | A | 8/2011 |
| JP | 2014192186 | A | 10/2014 |
| JP | 2015072978 | A | 4/2015 |
| JP | 2015092616 | A | 5/2015 |
| JP | 2016174024 | A | 9/2016 |
| WO | 2017141996 | A1 | 8/2017 |

OTHER PUBLICATIONS

Written Opinion (PCT/ISA/237) dated May 1, 2018, by the Japan Patent Office as the International Searching Authority for International Application No. PCT/JP2018/008313.

\* cited by examiner

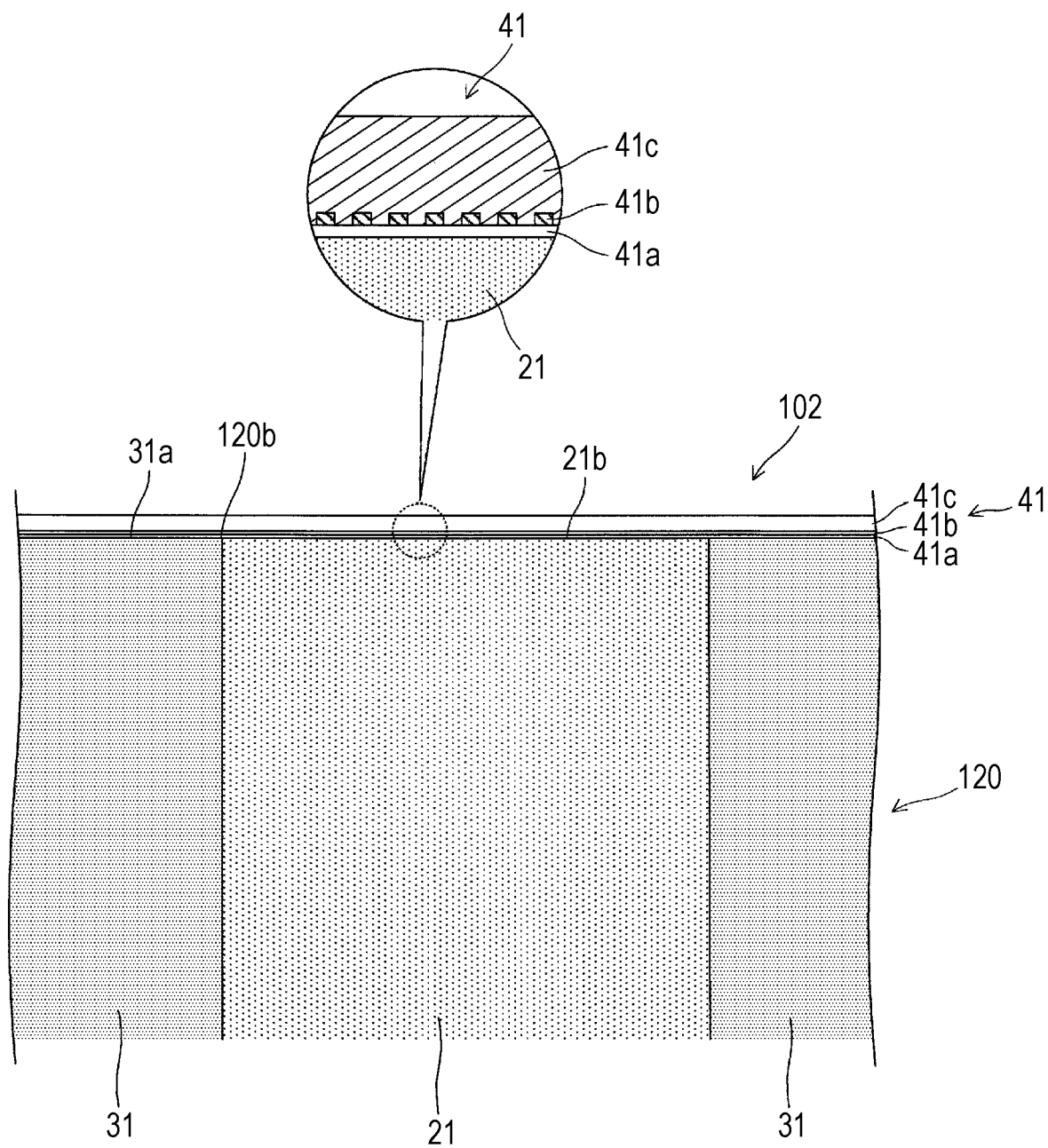

PIEZOELECTRIC MEMBER, ULTRASONIC OSCILLATION ELEMENT, ULTRASONIC PROBE, ULTRASOUND DIAGNOSTIC SYSTEM, AND METHOD FOR PRODUCING PIEZOELECTRIC MEMBER

TECHNICAL FIELD

The present invention relates to a piezoelectric member usable in an ultrasonic measuring device and other various ultrasonic applied devices, an ultrasonic oscillation element, an ultrasonic probe, and an ultrasound diagnostic system that include the piezoelectric member, and a method for producing the piezoelectric member.

BACKGROUND ART

A known piezoelectric member includes: a film containing a thiol group-containing compound on a piezoelectric element; and a metal electrode that is formed on the thiol compound film and is made of Au, Ni, or Pt (see Patent Literatures 1 and 2). A thiol compound film is used to enhance the strength of connection between a piezoelectric element and an electrode. Further, a metal electrode made of Au or the like has a low film stress, and is used to reduce inhibition of displacement of a piezoelectric element.

However, in a case where a thiol compound film is provided between a piezoelectric element and a metal electrode, the adhesiveness of the metal electrode to the piezoelectric element tends to become lower.

CITATION LIST

Patent Literatures

Patent Literature 1: JP 2015-72978 A
Patent Literature 2: JP 2015-92616 A

SUMMARY OF INVENTION

The present invention has been made in view of the above background art, and aims to provide a piezoelectric member in which a metal electrode has higher adhesiveness to a piezoelectric element.

The present invention also aims to provide an ultrasonic oscillation element, an ultrasonic probe, and an ultrasound diagnostic system that include a piezoelectric member in which a metal electrode has higher adhesiveness to a piezoelectric element.

The present invention further aims to provide a method for producing a piezoelectric member in which a metal electrode has higher adhesiveness to a piezoelectric element.

To achieve at least one of the above objects, a first piezoelectric member reflecting one aspect of the present invention includes: a piezoelectric element having two opposing surfaces; and two electrodes respectively formed on the two opposing surfaces of the piezoelectric element. At least one of the two electrodes includes: a base film that is formed on the corresponding one of the opposing surfaces and contains a thiol group-containing material; a metal adhesive film formed on the base film; and an electrode film that is formed on the metal adhesive film and is for applying voltage to the piezoelectric element. The metal adhesive film is formed with a material different from the electrode film, and has a thickness of 1 to 10 nm.

Further, to achieve at least one of the above objects, a second piezoelectric member reflecting one aspect of the present invention includes: a piezoelectric element having two opposing surfaces; and two electrodes respectively formed on the two opposing surfaces of the piezoelectric element. At least one of the two electrodes includes: a base film that is formed on the corresponding one of the opposing surfaces and contains a thiol group-containing material; a metal adhesive film formed on the base film; and an electrode film that is formed on the metal adhesive film and is for applying voltage to the piezoelectric element. The metal adhesive film is formed with a material different from the electrode film, and is distributed in the form of islands.

Further, to achieve at least one of the above objects, an ultrasonic oscillation element reflecting one aspect of the present invention includes the above piezoelectric member.

Further, to achieve at least one of the above objects, an ultrasonic probe reflecting one aspect of the present invention includes the above ultrasonic oscillation element, and a drive circuit that drives the ultrasonic oscillation element.

Further, to realize at least one of the above objects, an ultrasound diagnostic system reflecting one aspect of the present invention includes the above ultrasonic probe, and a control device that controls operation of the ultrasonic probe and receives a detection signal generated by the ultrasonic probe.

Further, to achieve at least one of the above objects, a method for producing a first piezoelectric member reflecting one aspect of the present invention is a method for producing a piezoelectric member that includes a piezoelectric element, and two electrodes respectively formed on two opposing surfaces of the piezoelectric element. The method includes: forming a base film on at least one of the two opposing surfaces of the piezoelectric element, the base film containing a thiol group-containing material; forming a metal adhesive film in a form of islands on the base film; and forming an electrode film on the metal adhesive film, the electrode film being formed with a different material from the metal adhesive film and being for applying voltage to the piezoelectric element.

Further, to achieve at least one of the above objects, a method for producing a second piezoelectric member reflecting one aspect of the present invention is a method for producing a piezoelectric member that includes a piezoelectric element, and two electrodes respectively formed on two opposing surfaces of the piezoelectric element. The method includes: forming a base film on at least one of the two opposing surfaces of the piezoelectric element, the base film containing a thiol group-containing material; forming a metal adhesive film having a thickness of 1 to 10 nm on the base film; and forming an electrode film on the metal adhesive film, the electrode film being formed with a different material from the metal adhesive film and being for applying voltage to the piezoelectric element.

BRIEF DESCRIPTION OF DRAWINGS

FIG. 3 is a conceptual cross-sectional view for explaining the structure of an electrode.

DESCRIPTION OF EMBODIMENTS

The following is a description of a piezoelectric member or an ultrasonic oscillation element that is an embodiment of the present invention, and a method for producing the piezoelectric member or the ultrasonic oscillation element, with reference to the drawings.

Figure 1:
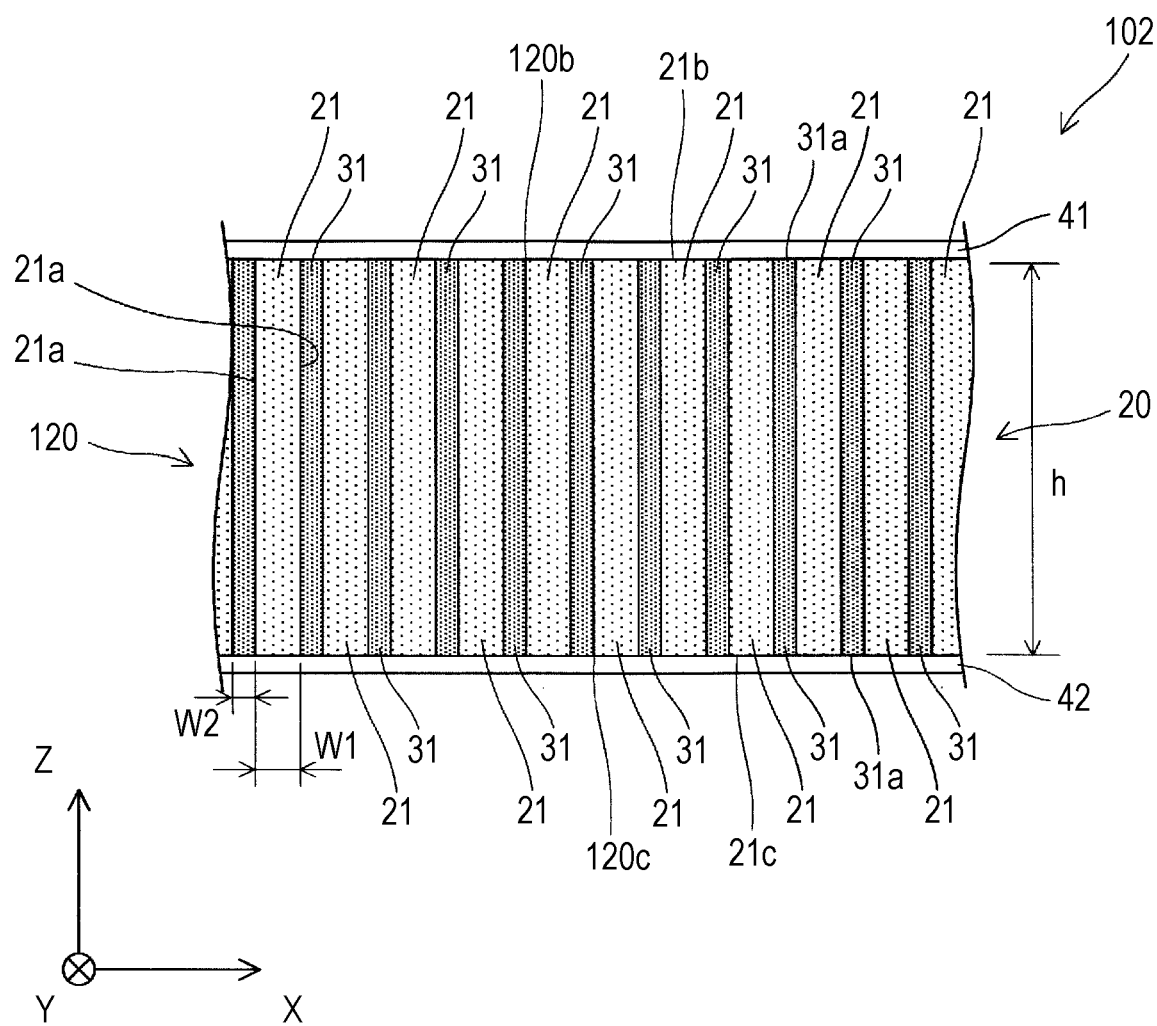
FIG. 1 is an enlarged cross-sectional view for explaining a piezoelectric member according to an embodiment of the present invention.
Figure 2A:
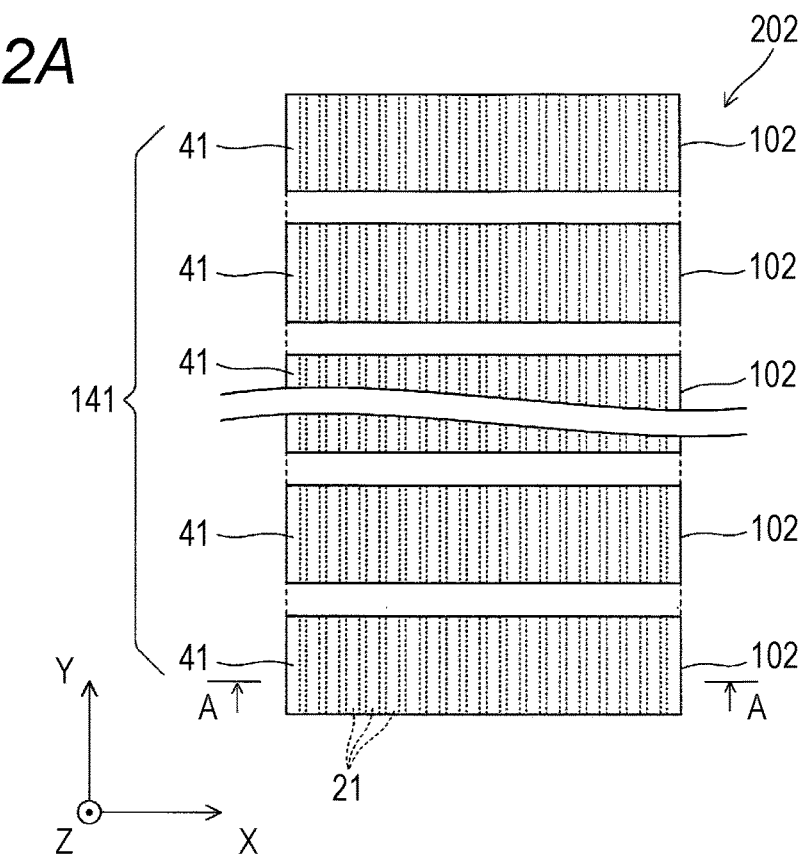
FIGS. 2A through 2C are a plan view, an A-A cross-sectional view, and a side view for explaining an ultrasonic oscillation element including the piezoelectric member shown in FIG. 1.
Figure 2B:
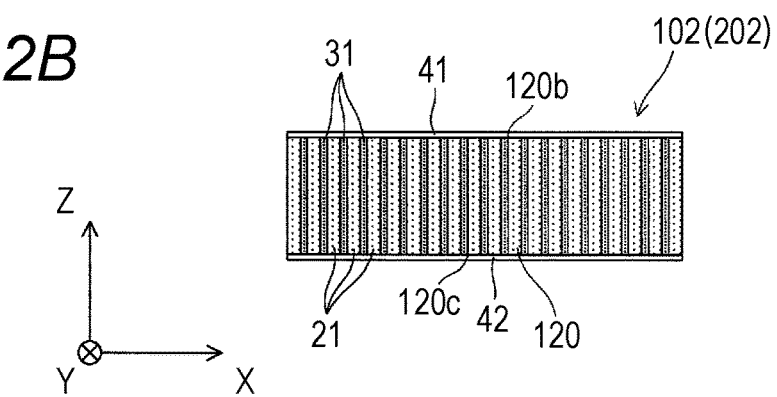
Figure 2C:
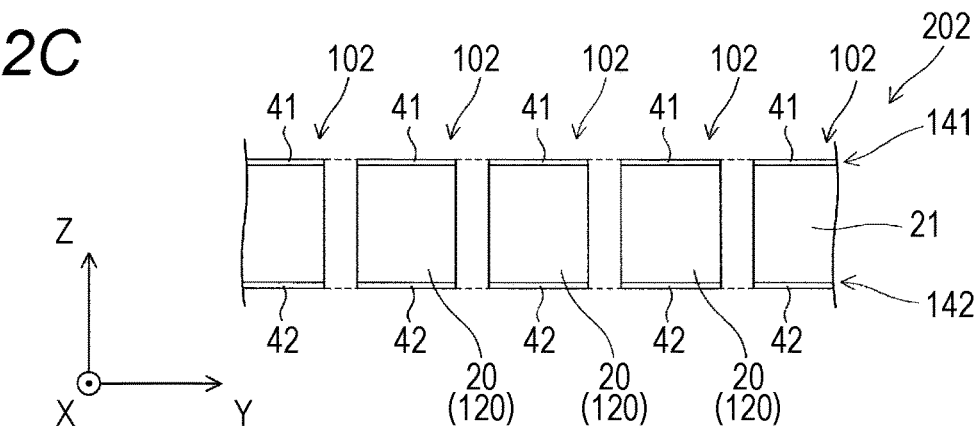
Figure 4A:
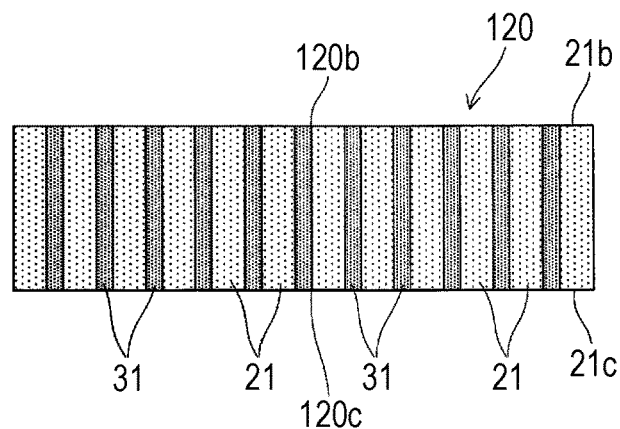
FIGS. 4A through 4D are diagrams for explaining a method for producing a piezoelectric member.
Figure 4B:
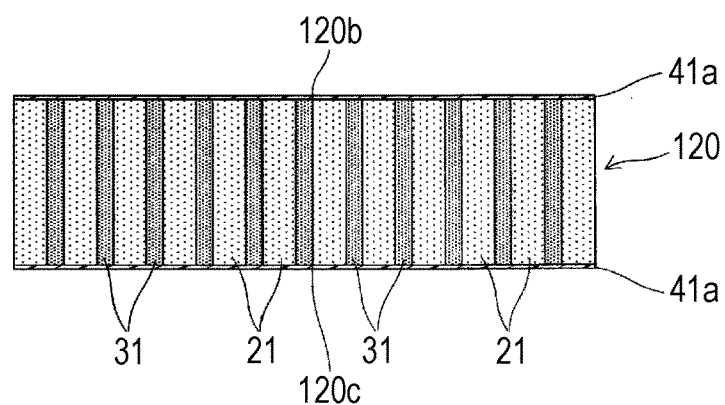
Figure 4C:
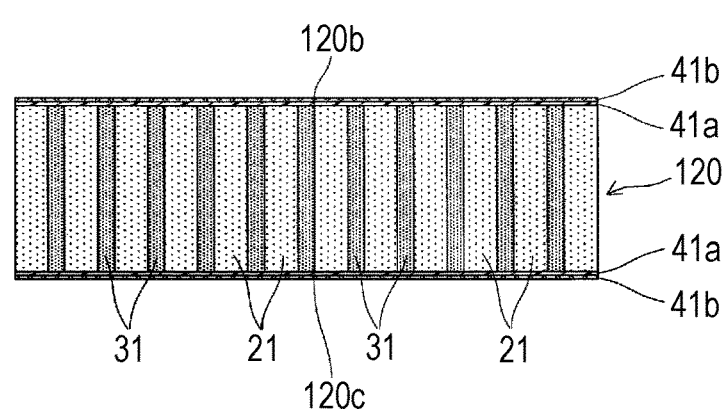
Figure 4D:
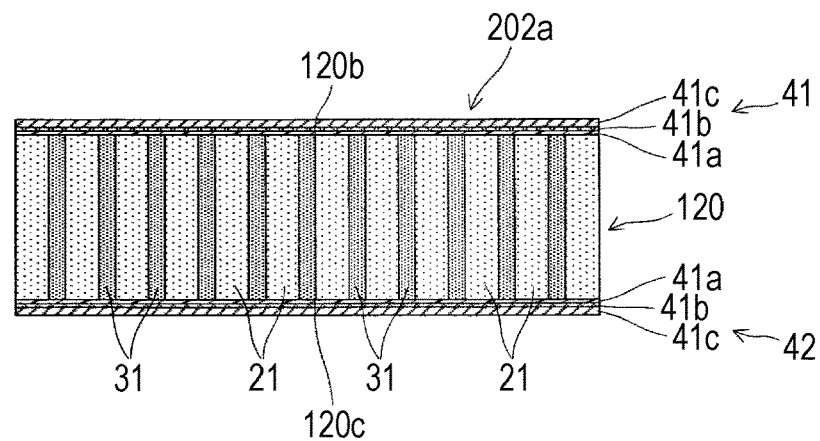

FIG. 1 is an enlarged cross-sectional view of a piezoelectric member of the embodiment. FIGS. 2A through 2C are a plan view, a cross-sectional view, and the like for explaining an ultrasonic oscillation element that is an assembly obtained by combining a plurality of piezoelectric members shown in FIG. 1.

As shown in FIG. 1, an individual piezoelectric member 102 includes a three-dimensional structure group 20 in which a plurality of piezoelectric elements 21 are periodically arranged, a large number of filler portions 31 filling the gaps in the three-dimensional structure group 20, and first and second electrodes 41 and 42 provided at the upper and lower sides of the three-dimensional structure group 20. Here, the three-dimensional structure group 20 is an array formed with the plurality of piezoelectric elements 21. A combination of the three-dimensional structure group 20 and the filler portions 31 filling the gaps, which is a structural body having a composite structure in which the electrodes 41 and 42 are excluded from the piezoelectric member 102, will be hereinafter referred to as the composite piezoelectric body 120. The composite piezoelectric body 120 is a rectangular or plate-like member that has a relatively long rectangular outline in the X direction in an X-Y plane and is thin in the Z direction. The first electrode 41 in the form of a thin film is formed on and joined onto the upper opposing surface 120$b$ of the composite piezoelectric body 120, and the second electrode 42 in the form of a thin film is formed on and joined onto the lower opposing surface 120$c$ of the composite piezoelectric body 120.

An ultrasonic oscillation element 202 shown in FIGS. 2A through 2C is formed by arranging a large number of block-like piezoelectric members 102 each having the structure shown in FIG. 1 in proximity to one another in the Y direction. In a broad sense, the ultrasonic oscillation element 202 can be regarded as a piezoelectric member. The individual piezoelectric members 102 constituting the ultrasonic oscillation element 202 are secured so as to maintain the mutual positional relationship by a support or an adhesive (not shown).

The piezoelectric elements 21 constituting the three-dimensional structure group 20 of each piezoelectric member 102 is made of a single-crystal material, and specifically, is made of a solid-solution single-crystal material. As the piezoelectric elements 21 are made of an appropriate single-crystal material, the piezoelectric member 102 having relatively great piezoelectric characteristics can be obtained. Specific examples of the material that can form the piezoelectric elements 21 include lead magnesium niobate titanate (PMN-PT), lead zirconate titanate (PZT), and other Pb-based piezoelectric materials (including PMNT, PIMNT, and PSMNT, for example). Here, PMN-PT is formed with PbO—MgO—Nb$_2$O$_5$—TiO$_2$, and contains 69.9 to 70.6 mass % of lead oxide, 2.5 to 3.1 mass % of magnesium oxide, 16.8 to 20.3 mass % of niobium oxide, and 6.7 to 10.1 mass % of titanium oxide, for example. The three-dimensional structure group 20 is formed with a large number of piezoelectric elements 21 formed in the form of thin plates or walls, and has a structure in which the piezoelectric elements 21 are arranged in one direction in an overlapping manner. The large number of piezoelectric elements 21 extends like thin plates in the Y direction in the depth direction and the Z direction in a vertical direction, and are arranged at substantially equal intervals in the X direction. Each piezoelectric element 21 has substantially the same shape, and has a rectangular outline close to that of a square when viewed in a cross-section parallel to a Y-Z plane.

The opposing surface 21$b$ of each piezoelectric element 21 has a side of 100 μm or shorter. Here, a side means the short side in a case where each piezoelectric element 21 does not have square end faces but has rectangular end faces. Specifically, each piezoelectric element 21 is 100 μm or smaller in the width (also referred to as the horizontal width) W1 in a cross-section parallel to a side of the opposing surface 21$b$ or to an X-Z plane, and the horizontal width is set at about 5 to 30 μm, for example. Further, the height (also referred to as the depth) h of each piezoelectric element 21 in a cross-section parallel to an X-Z plane is set at about 60 to 300 μm, for example. Note that the distance W2 between adjacent piezoelectric elements 21 (or the thickness of each filler portion 31) is not particularly limited, but is set at about 1 to 30 μm, for example.

The filler portions 31 are made of epoxy resin, for example, and, together with the large number of piezoelectric elements 21, integrally constitute the composite piezoelectric body 120, while maintaining ultrasonic isolation and insulation between the individual piezoelectric elements 21. The large number of piezoelectric elements 21 are supported by the filler portions 31 via the side surface 21$a$ thereof. By virtue of the existence of the filler portions 31, each piezoelectric element 21 is electrically independent of the adjacent piezoelectric elements 21, and an interaction does not easily occur in terms of ultrasonic waves.

As shown in FIGS. 2A through 2C, in the ultrasonic oscillation element 202, a group of first electrodes 41 extends in the X direction along the upper opposing surfaces 120$b$ of a large number of composite piezoelectric bodies 120, and forms a comb-like electrode 141 as a whole. Likewise, a group of second electrodes 42 also extends in the X direction along the lower opposing surfaces 120$c$ of the large number of composite piezoelectric bodies 120, and forms a comb-like electrode 142 as a whole. Note that 192 channels of composite piezoelectric bodies 120 and the first and second electrodes 41 and 42 sandwiching the composite piezoelectric bodies 120 are present in the Y direction, for example, and the 192 channels of composite piezoelectric bodies 120 receive drive signals independently of one another, for example. That is, individual drive signals having different timings and the like are supplied to the respective piezoelectric members 102.

FIG. 3 is a conceptual cross-sectional diagram for explaining the structure of the first electrode 41. The first electrode 41 is a multilayer film, and is formed on the opposing surfaces 21$b$ that are surfaces of the piezoelectric elements 21 and on surfaces 31$a$ of the filler portions 31. The first electrode 41 includes a base formed with a base film 41$a$ containing a thiol group-containing material, and also includes a metal adhesive film 41b formed on the base film 41a, and an electrode film 41c that is formed on the metal adhesive film 41b and is for applying voltage to the piezoelectric elements 21.

The base film 41a has a thickness of molecular size, and (3-mercaptopropyl)trimethoxysilane may be used as the thiol group-containing compound that forms the base film 41a. For example, the mercapto group-containing polymer disclosed in JP 10-77311 A, or a thiol group-containing polymer, may also be used as the thiol group-containing compound that forms the base film 41a. Specifically, it is possible to use a thiol group-containing polymer (corresponding to the mercapto group-containing polymer disclosed in claim 1 of JP 10-77311 A) that has, in its main chain, a structural unit expressed by the following general formula (1) or (2):

$$—CH(SH)—CH(SH)— \quad (1)$$

$$—CH_2—C(SH)(SH)— \quad (2)$$

Alternatively, it is possible to use a thiol group-containing polymer (corresponding to the mercapto group-containing polymer disclosed in claim 2 of JP 10-77311 A) obtained by causing a hydrosulfide of an alkali metal to react with a chlorinated polyethylene that has, in its main chain, a structural unit expressed by the following general formula (3) or (4):

$$—CH(Cl)—CH(Cl)— \quad (3)$$

$$—CH_2—C(Cl)(Cl)— \quad (4)$$

The metal adhesive film 41b is added from the viewpoint of improvement of adhesiveness to the electrode film 41c, and is made of Cr, Pt, Pd, In, or the like. The metal adhesive film 41b has a thickness of 1 to 10 nm. Having a thickness of 1 to 10 nm, the metal adhesive film 41b is formed in the form of islands. As the metal adhesive film 41b is distributed in the form of islands, the metal adhesive film 41b is disposed at intervals along the opposing surfaces 21b, and thus, the influence of piezoelectric deformation inhibition by the electrodes 41 is reduced. That is, in a case where the thickness of the metal adhesive film 41b is 1 to 10 nm, or the metal adhesive film 41b is formed in the form of islands, the rigidity of the metal adhesive film 41b is prevented from increasing, and deformation along the surfaces along which the electrode 41 extends becomes relatively easy. The metal adhesive film 41b is formed by a physical film formation method, or specifically, a sputtering method. As the metal adhesive film 41b is formed by a sputtering method, it becomes easier to increase the density of the islands of the metal adhesive film 41b.

The thickness of the metal adhesive film 41b may be measured by a measurement method using a sputtering depth profile, a focused ion beam (FIB) processing apparatus, or the like. In a case where a sputtering depth profile is used, surface analysis is repeated while ion etching is performed. The depth direction analysis method to be used herein may be X-ray photoelectron spectroscopy (XPS), Auger electron spectroscopy (AES), time-of-flight secondary ion mass spectrometry (TOF-SIMS), or the like. In a case where an FIB is used, a thin cross-section is prepared with the FIB, and is observed with a transmission electron microscope (TEM).

The electrode film 41c has a conductivity of a predetermined level or higher, and is made of Au, Pt, Ag, Ni, or the like. The electrode film 41c has a thickness of 0.05 to 1 μm.

The electrode film 41c can be formed by various physical film formation methods or chemical film formation methods. For example, the electrode film 41c can be formed by a film formation method such as plating, sputtering, or vapor deposition. The material of the electrode film 41c is preferably selected depending on the material of the metal adhesive film 41b. Specifically, example combinations of an electrode film/a metal adhesive film include Au/Cr, Au/Ti, Au/In, Pt/Ti, Pt/Pd, Ni/Cr, and Ag/Cr. With such a combination, the electrode film 41c adheres to the base film 41a or the piezoelectric elements 21 with sufficient strength via the metal adhesive film 41b.

The second electrode 42 has the same structure as the first electrode 41, though not specifically described. However, the base film, the metal adhesive film, and the electrode film that constitute the second electrode 42 are not necessarily made of the same materials as those of the base film 41a, the metal adhesive film 41b, and the electrode film 41c that constitute the first electrode 41.

Referring now to FIGS. 4A through 4D, a method for producing the piezoelectric member 102 and the ultrasonic oscillation element 202 shown in FIG. 1A and the like is described. First, to obtain a large number of piezoelectric elements 21, a bulk material is cut with a dicing saw or the like so that a large number of thin plate-like precursors are prepared. The large number of thin plate-like precursors are then immersed in an etching solution containing a fluoride or the like, and the surfaces of the thin plate-like precursors are subjected to wet etching, so that the portions to be the piezoelectric elements 21 are obtained. An epoxy resin or some other resin adhesive with an appropriate viscosity is supplied to the portions between the portions to be the piezoelectric elements 21 stacked in layers. After that, the piezoelectric elements 21 stacked in layers are pressed from both sides with an appropriate pressure, to adjust the thickness of the resin adhesive to the target value and to harden the resin adhesive. As a result, a composite piezoelectric body 120 in which a large number of piezoelectric elements 21 and a large number of filler portions 31 are alternately stacked is obtained (see FIG. 4A). Note that grounding and polishing are performed on the composite piezoelectric body 120, to form a pair of opposing surfaces 120b and 120c. The pair of opposing surfaces 120b and 120c includes the pair of opposing surfaces 21b and 21c of each piezoelectric element 21.

After that, the first and second electrodes 41 and 42 are formed on the pair of opposing surfaces 120b and 120c of the composite piezoelectric body 120. Specifically, the base film 41a is first formed. That is, the composite piezoelectric body 120 is immersed in a solution obtained by diluting a thiol group-containing polymer ((3-mercaptopropyl)trimethoxysilane, for example) with water, alcohol, and acetic acid, and the composite piezoelectric body 120 is pulled out from the solution. After being left in a drying furnace for a predetermined time, the composite piezoelectric body 120 is taken out of the drying furnace, and is washed with running water. The composite piezoelectric body 120 is then put back in the drying furnace, and is dried. As a result, the base film 41a is formed on the pair of opposing surfaces 120b and 120c (see FIG. 4B). The metal adhesive film 41b is then formed on the base film 41a. That is, a metallic material such as Cr, Pt, Pd, or In is formed into a film of 1 to 10 nm in thickness on the base film 41a by a sputtering method (see FIG. 4C). With this thickness, the metallic material such as Cr, Pt, Pd, or In is formed into small separate pieces in the form of islands, and the metal adhesive film 41b is not continuous like a layer with a uniform thickness, but is discontinuous in a lateral direction. Lastly, the electrode film 41c is formed. That is, a metallic material such as Au, Pt, Ag, Ni, or the like is formed into a layer of 0.05 to 1 μm in thickness on the metal adhesive film 41b by a physical film formation method or a chemical vapor deposition method (see FIG. 4D). The first and second electrodes 41 and 42 are formed concurrently in the example shown in the drawings, but the two electrodes may be formed individually. The composite piezoelectric body 120 in which the first and second electrodes 41 and 42 are formed in this manner will be hereinafter referred to as the ultrasonic oscillation element base material 202a.

Lastly, the composite piezoelectric body 120 in which the first and second electrodes 41 and 42 are formed, which is the ultrasonic oscillation element base material 202a, is divided in the Y direction parallel to an X-Z plane with a dicing device or the like, so that a plurality of piezoelectric members 102 are obtained (see FIGS. 2A through 2C). A large number of piezoelectric members 102 obtained from one or more ultrasonic oscillation element base materials 202a constitute an ultrasonic oscillation element 202. Note that the specific number of piezoelectric elements 21 included in a piezoelectric member 102 and arranged in the X direction is about several tens to several hundreds, for example. A specified number of piezoelectric members 102 among the large number of piezoelectric members 102 obtained as above are arranged in the Y direction and are fixed to one another, so that an ultrasonic oscillation element 202 is obtained.

In the description below, specific examples of methods of manufacturing a piezoelectric member or an ultrasonic oscillation element are explained. As for the common aspects in the examples, a block-like bulk material for a piezoelectric element, or a composite structure in which the portions between piezoelectric elements arranged in an array are filled with resin was used as the base material portion excluding the electrodes from a piezoelectric member. PMN-PT was used as the material of the piezoelectric elements, and epoxy resin was used as the filler resin. Meanwhile, the base film was formed with (3-mercaptopropyl)trimethoxysilane. Specifically, a composite piezoelectric body was immersed, for five minutes, in a solution prepared by mixing 0.056 g of (3-mercaptopropyl)trimethoxysilane, 0.005 g of acetic acid, 6.1 g of water, and 1 g of ethanol, and stirring for 60 minutes. After being left in a drying furnace at 60° C. for 20 minutes, the composite piezoelectric body was taken out, was washed with running water for three minutes, and was then dried in the drying furnace at 50° C. for 15 minutes. The metal adhesive film was formed by a sputtering method using Cr as the material. The electrode film was formed by vapor deposition using Au as the material. Note that the metal adhesive film and the electrode film were both formed by sputtering under the conditions that the RF output was 150 W, the process pressure was 0.3 Pa, and the argon gas flow rate was 20 sccm. The film formation time for the former film was 20 to 300 seconds (2 to 30 nm), and the film formation time for the latter film was 2970 seconds (450 nm). The piezoelectric member obtained as above was diced, and the peeling states of the electrodes were observed with an optical microscope. Table 1 shown below summarizes the results.

TABLE 1

| | | Film configuration, thickness [nm] | | | Dicing test result | |
|---|---|---|---|---|---|---|
| | Piezoelectric member | Base film (thiol group-containing film) | Metal adhesive film (Cr) | Electrode film (Au) | Evaluation | Explanation of evaluation |
| Example 1 | PMN-PT single crystal | present | 2 | 450 | ○ | no peeling |
| Example 2 | PMN-PT single crystal Epoxy resin | present | 2 | 450 | ○ | no peeling |
| Example 3 | PMN-PT single crystal Epoxy resin | present | 8 | 450 | ○ | no peeling |
| Example 4 | PMN-PT single crystal | present | 10 | 450 | Δ | slightly peeled but no problem for practical use |
| Comparative Example 1 | PMN-PT single crystal Epoxy resin | not present | 2 | 450 | X | partially peeled |
| Comparative Example 2 | PMN-PT single crystal | not present | 8 | 450 | X | partially peeled |
| Comparative Example 3 | PMN-PT single crystal | not present | 12 | 450 | XX | peeled before dicing |
| Comparative Example 4 | PMN-PT single crystal | not present | 30 | 450 | XX | peeled before dicing |
| Comparative Example 5 | PMN-PT single crystal | present | 30 | 450 | X | partially peeled |
| Comparative Example 6 | PMN-PT single crystal Epoxy resin | present | 30 | 450 | X | partially peeled |
| Comparative Example 7 | PMN-PT single crystal | present | 12 | 450 | X | partially peeled |

As is apparent from Table 1 shown above, electrodes that do not easily peel off can be formed by dicing, where a thiol group-containing film is used as the base film, and a Cr film of about 2 to 10 nm in thickness is formed as the metal adhesive film on the base film.

Figure 5A:
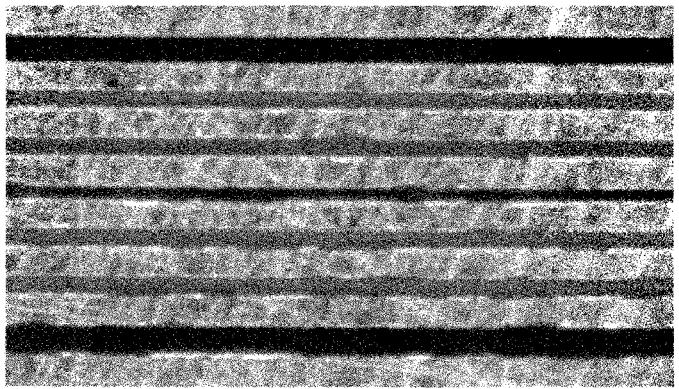
FIG. 5A shows a state of an electrode in a piezoelectric member of an example.
Figure 5B:
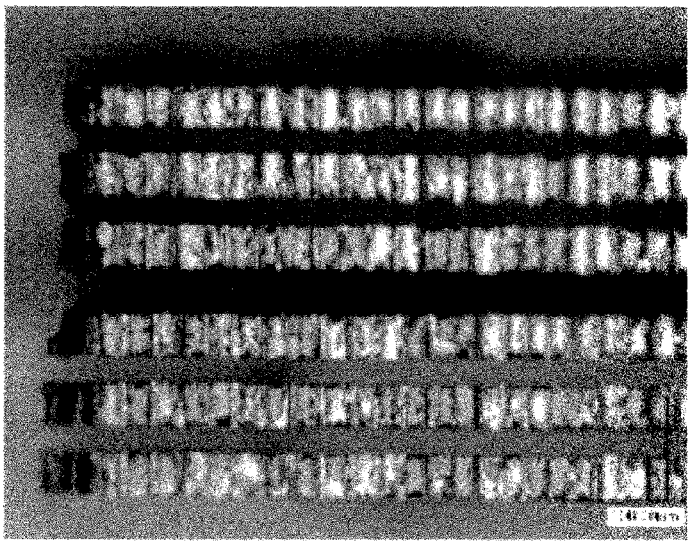
FIG. 5B shows a state of an electrode in a piezoelectric member of a comparative example.
Figure 5C:
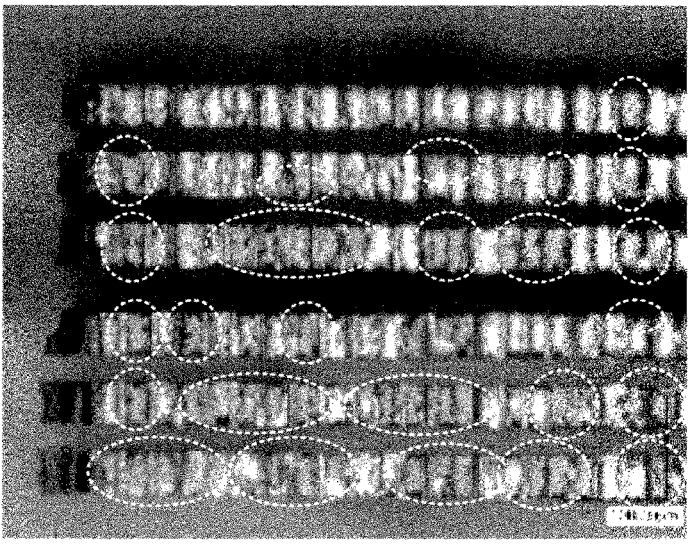
FIG. 5C shows a state of an electrode like FIG. 5B, and also indicates peeling portions.

FIG. 5A shows an electrode surface of the piezoelectric member of Example 3, and no peeling has occurred in the electrode. Further, FIG. 5B shows an electrode surface of the piezoelectric member of Comparative Example 1, and partial peeling has occurred in the electrode. Note that FIG. 5C is a diagram created by adding marks to FIG. 5B, and the portions in the circles indicated by dashed lines are portions where peeling has occurred.

Figure 6:
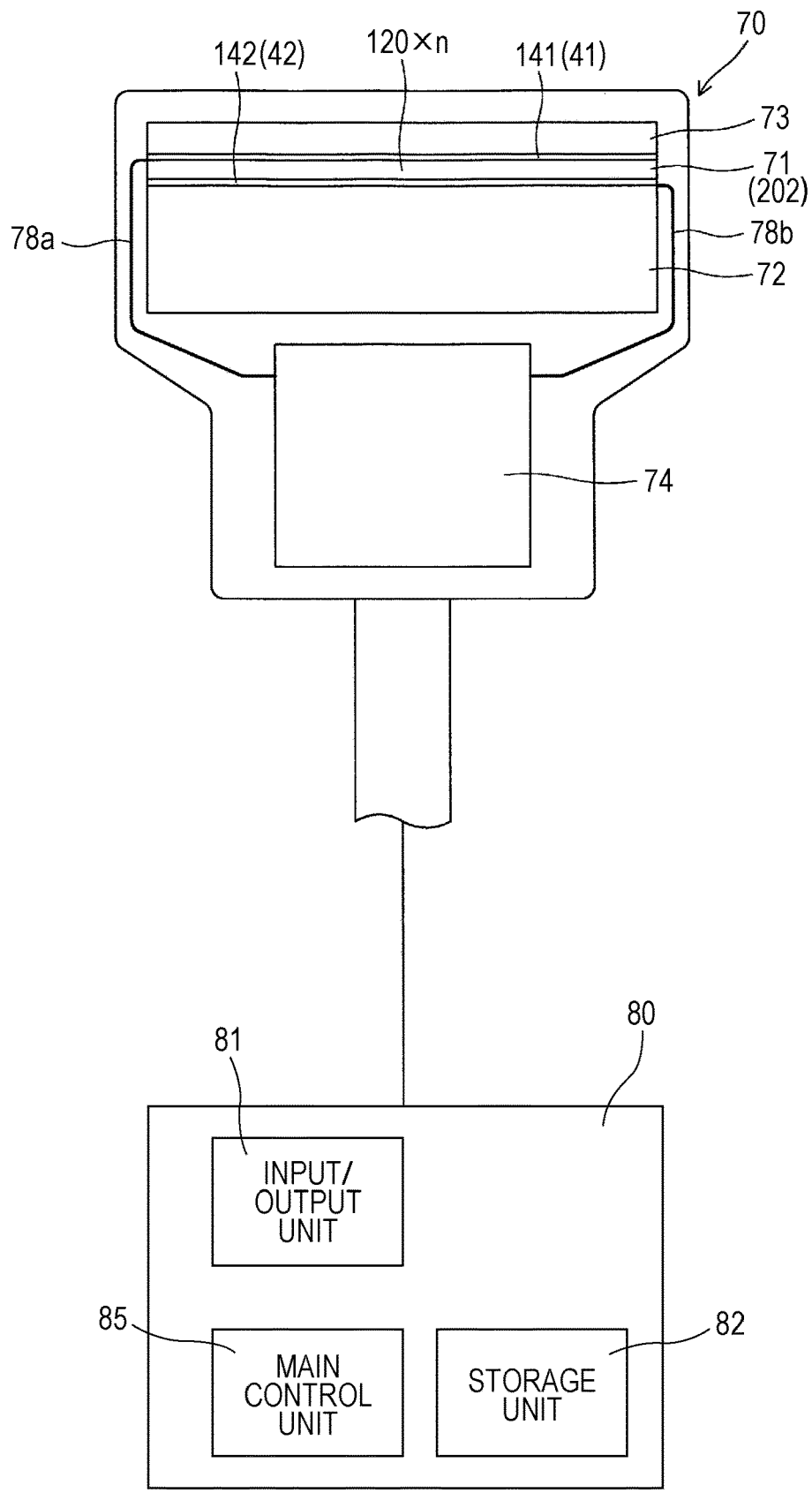
FIG. 6 is a conceptual diagram for explaining an ultrasonic probe and an ultrasound diagnostic system into which the ultrasonic oscillation element shown in FIG. 2 is incorporated.

FIG. 6 is a diagram for explaining an ultrasonic probe and an ultrasound diagnostic system manufactured using the ultrasonic oscillation element 202 shown in FIG. 2A and the like.

An ultrasound diagnostic system 100 includes an ultrasonic probe 70 and a control device 80. The ultrasonic probe 70 includes a vibrating portion 71 including the ultrasonic oscillation element 202, a backing material 72 disposed behind the vibrating portion 71, a matching layer 73 disposed on the front surface of the vibrating portion 71, and a drive circuit 74 that operates the vibrating portion 71. The ultrasonic oscillation element 202 forming the vibrating portion 71 includes a specified number n (specifically, 128 channels, for example) of composite piezoelectric bodies 120 arranged in the lateral direction in the drawing, and comb-like electrodes 141 and 142 sandwiching these composite piezoelectric bodies 120 from the upper and lower sides. The comb-like electrode 141 is a positive electrode, for example, and has each first electrode 41 connected to a ribbon-like parallel wiring line 78a. The other comb-like electrode 142 is a negative electrode, for example, and has each second electrode 42 connected to a ribbon-like parallel wiring line 78b. Both parallel wire lines 78a and 78b extend from the drive circuit 74, and apply a voltage having a period corresponding to ultrasonic waves to the unit probe or pixel (corresponding to the piezoelectric member 102 shown in FIG. 1) corresponding to each channel, to cause ultrasonic vibration in the large number of piezoelectric elements 21 constituting the piezoelectric member 102, and the ultrasonic vibration received in the large number of piezoelectric elements 21 is converted into a voltage signal. Note that the backing material 72 prevents ultrasonic waves from being emitted to the rear side of the vibrating portion 71. Further, the matching layer 73 has a role of reducing reflection of ultrasonic waves entering or exiting the front side of the vibrating portion 71.

The control device 80 includes an input/output unit 81, a storage unit 82, and a main control unit 85. The input/output unit 81 includes an interface circuit with the ultrasonic probe 70, a display keyboard for the user, and the like. The storage unit 82 stores programs and data for operating the ultrasonic probe 70, and can also record measurement results obtained with the ultrasonic probe 70. The main control unit 85 causes the ultrasonic probe 70 to perform operations to transmit or receive ultrasonic waves, on the basis of user instructions.

Specific operations of the ultrasonic probe 70 and the ultrasound diagnostic system 100 are now described. The ultrasound diagnostic system 100 alternately repeats an ultrasonic wave transmission operation to be performed in a nanosecond to microsecond period, and an ultrasonic wave reception operation to be performed in a similar period. In a transmission operation, the drive circuit 74 receives a trigger signal from the control device 80, and causes ultrasonic vibration at a predetermined delay time that is set in each of the piezoelectric members 102 constituting the ultrasonic probe 70. In a reception operation, the drive circuit 74 receives a voltage signal corresponding to ultrasonic wave reflection detected by each of the piezoelectric members 102, and combines the signals at a predetermined delay time that is set in each of the piezoelectric members 102. This enables wavefront control for ultrasonic waves. As a result, ultrasonic waves of a desired frequency can be applied to a dot-like object located in front of the ultrasonic probe 70, and ultrasonic waves reflected back from the dot-like object can be selectively received and be turned into a detection signal. The main control unit 85 of the control device 80 can reconstruct a cross-sectional image or the like of the object from the detection signal obtained by the ultrasonic probe 70, and display the reconstructed image on the display of the input/output unit 81, for example.

In the piezoelectric members 102 incorporated into the ultrasonic probe 70 or the ultrasound diagnostic system 100 of the embodiment described above, the thickness of the metal adhesive film 41b inserted between the base film 41a made of a thiol group-containing material and the electrode film 41c for applying voltage to the piezoelectric elements 21 is 1 to 10 nm. Therefore, the metal adhesive film 41b is extremely thin, and is turned into island forms, for example. As a result, the rigidity of the electrode main body including the metal adhesive film 41b and the electrode film 41c becomes lower, and accordingly, the influence of piezoelectric deformation inhibition can be reduced. Meanwhile, because of the presence of the metal adhesive film 41b, the adhesiveness between the piezoelectric elements 21 and the electrode film 41c is improved in conjunction with adhesiveness enhancement by the base film 41a containing a thiol group, and peeling of the electrode film 41c can be prevented while the deformation amount of the piezoelectric elements 21 is maintained.

The structure in which the portions between the piezoelectric elements 21 are filled with resin is advantageous in increasing the sensitivity of the ultrasonic probe 70. Further, because of the structure in which the portions between the piezoelectric elements 21 are filled with resin, deformation in the plane directions of the electrodes 41 and 42 is reduced even in a case where the piezoelectric elements 21 are miniaturized. Thus, the electrodes 41 and 42 become more difficult to peel off. Note that, since resin does not undergo piezoelectric deformation, the film on the resin portions does not peel off.

Further, as the ultrasonic oscillation element 202 and the ultrasonic probe 70 include the above described piezoelectric members 102, the adhesiveness of the piezoelectric members 102 becomes higher, to improve durability, operation performance, manufacturing yield, and the like. Furthermore, the ultrasound diagnostic system 100 including the above described ultrasonic probe 70 can improve the accuracy of diagnosis with the ultrasonic probe 70.

Although the present invention has been described on the basis of embodiments so far, piezoelectric members and the like according to the present invention are not limited to those described above. For example, the specific examples of the horizontal width, the length in the depth direction, and the height (or the depth) of each piezoelectric element 21 are merely examples, and may be set as appropriate within the limits disclosed in the claims.

Figure 7A:
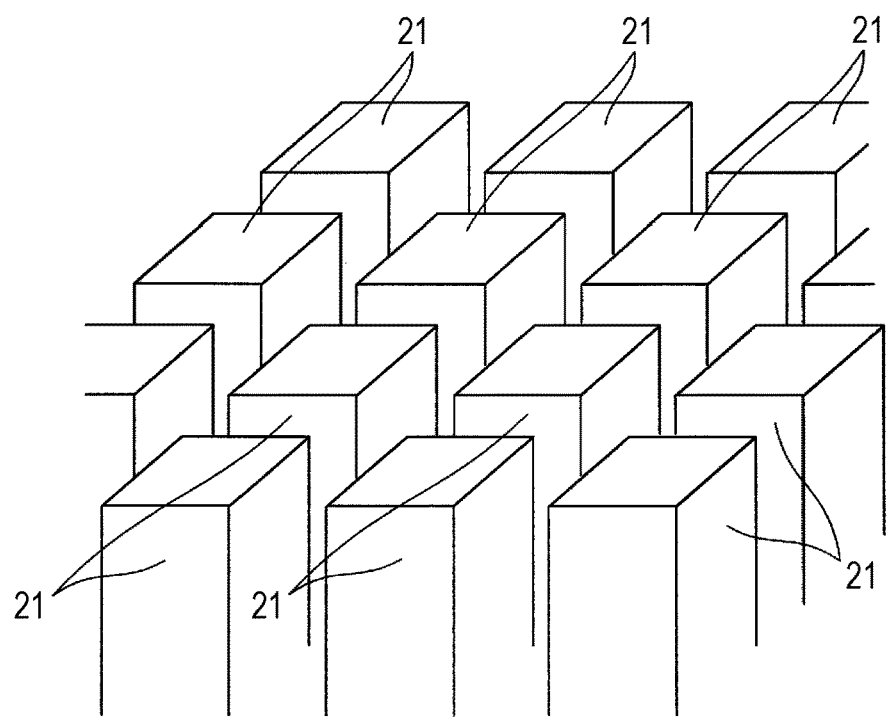
FIGS. 7A and 7B are conceptual perspective diagrams for explaining a piezoelectric member of a modification.
Figure 7B:
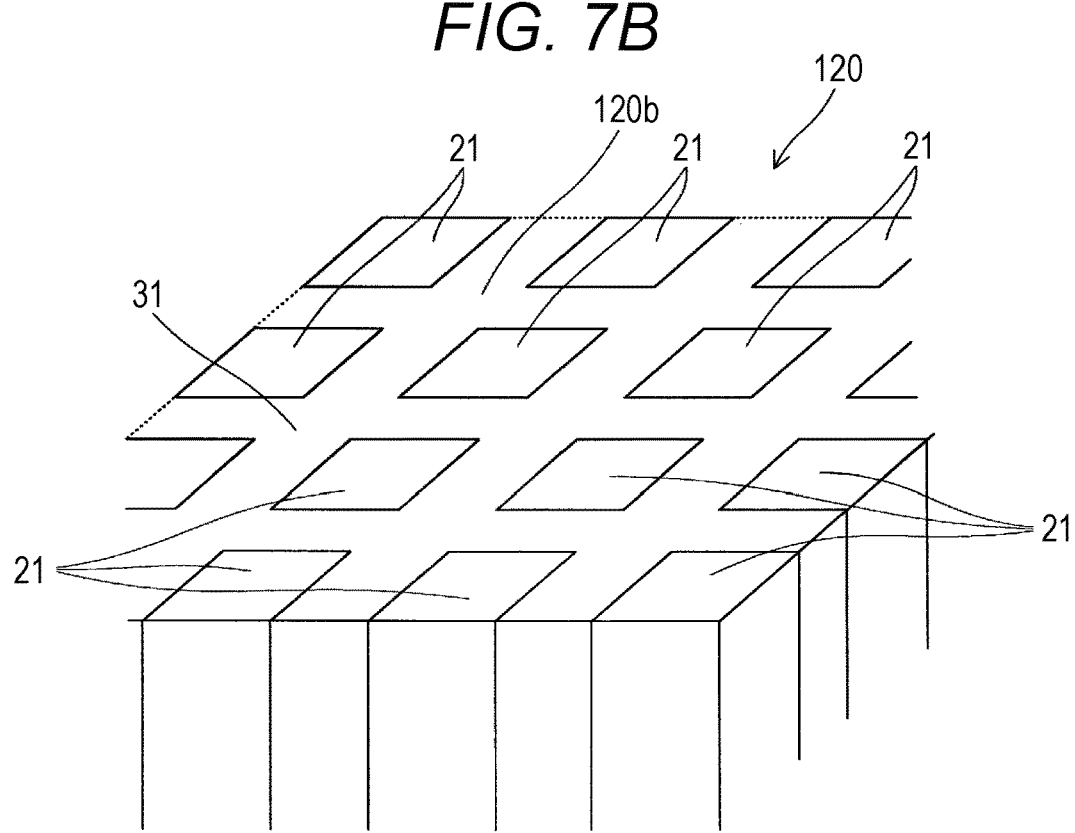

The piezoelectric elements 21 are not necessarily plate-like or wall-like ones arranged one-dimensionally as shown in FIGS. 2A and 2B, but piezoelectric elements 21 formed like square or rectangular columns when viewed in a plan view may be two-dimensionally arranged. That is, as shown partially in FIGS. 7A and 7B, for example, square-pillared piezoelectric elements 21 are two-dimensionally and periodically arranged, the gaps between these piezoelectric elements 21 are filled with filler portions 31, and the end faces are polished. In this manner, a composite piezoelectric body 120 having an opposing surface 120b (only one opposing surface is shown) is obtained. Although not shown in the drawings, the first electrode 41 is formed on the opposing surface 120b.

The electrode film 41c is not necessarily formed with a single metallic conductive film, but may be formed with a plurality of kinds of metallic conductive films that are laminated.

The first and second electrodes 41 and 42 are preferably made of the same material and have the same structure. However, the first and second electrodes 41 and 42 may be made of different materials and/or have different structures. For example, at least one of the electrode film, the metal adhesive film, and the base film may be different between the two electrodes, or the thickness of at least one of these films may be different between the two electrodes. Further, depending on the purpose of use or the like of the piezoelectric member, either one of the first and second electrodes 41 and 42 may include a metal adhesive film of a thickness greater than 10 nm, or may exclude the metal adhesive film.

The invention claimed is:

1. A piezoelectric member comprising:
   a piezoelectric element having two opposing surfaces; and
   two electrodes respectively formed on the two opposing surfaces of the piezoelectric element, wherein
   at least one of the two electrodes includes: a base film that is formed on the corresponding one of the opposing surfaces and contains a thiol group-containing material; a metal adhesive film formed on the base film; and an electrode film that is formed on the metal adhesive film and is for applying voltage to the piezoelectric element, and
   the metal adhesive film is formed with a material different from the electrode film, and has a thickness of 1 to 10 nm.

2. The piezoelectric member according to claim 1, wherein
   a plurality of the piezoelectric elements each having the two opposing surfaces are provided to form an array, the two opposing surfaces each having a side not longer than 100 μm, and
   a portion between adjacent ones of the piezoelectric elements forming the array is filled with resin.

3. The piezoelectric member according to claim 1, wherein the piezoelectric element is formed with a single-crystal material.

4. The piezoelectric member according to claim 1, wherein the base film is formed with (3-mercaptopropyl)trimethoxysilane.

5. The piezoelectric member according to claim 1, wherein the metal adhesive film is formed with a material selected from Cr, Pt, Pd, and In.

6. The piezoelectric member according to claim 1, wherein the metal adhesive film is distributed in a form of islands.

7. The piezoelectric member according to claim 2, wherein the piezoelectric element is formed with a single-crystal material.

8. The piezoelectric member according to claim 2, wherein the base film is formed with (3-mercaptopropyl)trimethoxysilane.

9. A piezoelectric member comprising:
   a piezoelectric element having two opposing surfaces; and
   two electrodes respectively formed on the two opposing surfaces of the piezoelectric element, wherein
   at least one of the two electrodes includes: a base film that is formed on the corresponding one of the opposing surfaces and contains a thiol group-containing material; a metal adhesive film formed on the base film; and an electrode film that is formed on the metal adhesive film and is for applying voltage to the piezoelectric element, and
   the metal adhesive film is formed with a material different from the electrode film, and is distributed in a form of islands.

10. An ultrasonic oscillation element comprising the piezoelectric member according to claim 1.

11. An ultrasonic probe comprising: the ultrasonic oscillation element according to claim 10; and a drive circuit that drives the ultrasonic oscillation element.

12. An ultrasound diagnostic system comprising: the ultrasonic probe according to claim 11; and a control device that controls operation of the ultrasonic probe, and receives a detection signal generated by the ultrasonic probe.

13. An ultrasonic oscillation element comprising the piezoelectric member according to claim 9.

14. A method for producing a piezoelectric member that includes a piezoelectric element, and two electrodes respectively formed on two opposing surfaces of the piezoelectric element,
   the method comprising:
   forming a base film on at least one of the two opposing surfaces of the piezoelectric element, the base film containing a thiol group-containing material;
   forming a metal adhesive film in a form of islands on the base film; and
   forming an electrode film on the metal adhesive film, the electrode film being formed with a different material from the metal adhesive film and being for applying voltage to the piezoelectric element.

15. The method for producing a piezoelectric member according to claim 14, wherein the metal adhesive film is formed on the base film by a sputtering method.

16. The method for producing a piezoelectric member according to claim 14, wherein a structure including: a plurality of piezoelectric elements each having two opposing surfaces with a side not longer than 100 μm and forming an array; and a resin filling a portion between adjacent ones of the piezoelectric elements is used as the piezoelectric element, and the two electrodes are formed on the structure.

17. The method for producing a piezoelectric member according to claim 14, wherein the piezoelectric element is formed with a single-crystal material.

18. The method for producing a piezoelectric member according to claim 14, wherein the base film is formed with (3-mercaptopropyl)trimethoxysilane.

19. The method for producing a piezoelectric member according to claim 14, wherein the metal adhesive film is formed with a material selected from Cr, Pt, Pd, and In.

20. A method for producing a piezoelectric member that includes a piezoelectric element, and two electrodes respectively formed on two opposing surfaces of the piezoelectric element,
   the method comprising:
   forming a base film on at least one of the two opposing surfaces of the piezoelectric element, the base film containing a thiol group-containing material;
   forming a metal adhesive film having a thickness of 1 to 10 nm on the base film; and
   forming an electrode film on the metal adhesive film, the electrode film being formed with a different material from the metal adhesive film and being for applying voltage to the piezoelectric element.

* * * * *